United States Patent [19]

Elmore

[11] Patent Number: 5,558,158
[45] Date of Patent: Sep. 24, 1996

[54] HYGIENIC AIR HANDLER

[76] Inventor: Robert L. Elmore, 900 NW. 8th Ave., Fort Lauderdale, Fla. 33311

[21] Appl. No.: 385,577

[22] Filed: Feb. 8, 1995

Related U.S. Application Data

[63] Continuation of Ser. No. 246,093, May 19, 1994, abandoned.

[51] Int. Cl.$^6$ .............................. F28F 13/12; F28F 19/02
[52] U.S. Cl. ...................... 165/122; 165/133; 55/267; 62/78; 62/264; 422/121
[58] Field of Search .................................. 165/133, 122; 55/267; 62/78, 264; 422/121; 502/5

[56] References Cited

U.S. PATENT DOCUMENTS

| | | | |
|---|---|---|---|
| 2,335,056 | 11/1943 | Grison | 165/122 X |
| 2,425,816 | 8/1947 | Maxson | 62/231 |
| 2,637,819 | 5/1953 | Mumma | 250/453.11 |
| 3,100,679 | 8/1963 | Kritzer | 422/121 |
| 3,105,733 | 10/1963 | Potapenko | 422/121 |
| 3,486,308 | 12/1970 | Burt | 55/270 |
| 3,518,046 | 6/1970 | Cicirello | 422/4 |
| 3,576,593 | 4/1971 | Cicirello | 422/4 |
| 3,827,862 | 8/1974 | Berlant | 422/121 |
| 3,846,072 | 11/1974 | Patterson | 422/121 |
| 4,955,208 | 9/1990 | Kawashima et al. | 62/264 |
| 4,990,313 | 2/1991 | Pacosz | 422/121 |
| 5,015,422 | 5/1991 | Hirai | 422/121 |
| 5,112,370 | 5/1992 | Gazzano | 422/121 |
| 5,207,074 | 5/1993 | Cox et al. | 62/285 |
| 5,225,167 | 7/1993 | Wetzel | 422/121 |
| 5,334,347 | 8/1994 | Hollander | 422/121 X |

*Primary Examiner*—Leonard R. Leo
*Attorney, Agent, or Firm*—James Creighton Wray

[57] ABSTRACT

Interior surfaces of an air handler unit are coated with a dense, non-porous material, which discourages and prohibits growth of mold, spores, algae, bacteria, germs, viruses and other organisms and microorganisms and allergens. Air is drawn into the air handler unit through a return duct and one or more filters, through a heat exchanger and into a blower within the air handler unit. The blower draws and discharges air through highly reflective, interiorly coated chambers, where the air is bathed with direct and reflected ultraviolet light. The clean, conditioned air is then delivered through main distribution and supply ducts.

4 Claims, 2 Drawing Sheets

HYGIENIC AIR HANDLER

This application is a File Wrapper continuation of Ser. No. 08/246,093, filed May 19, 1994, now abandoned.

BACKGROUND OF THE INVENTION

This invention is related to cleaning indoor air and to air handling units used in air conditioning and/or heating systems.

Inside the systems are a fan to move the air, an evaporator or cooling coil or a heating coil, and generally an electric motor with appropriate electrical connections to drive the fan. Inside air handler-units for air conditioning purposes there is also a pan and drain line to collect and drain the condensate, and for heating purposes there could be a pan without a drain to hold water to supply moisture to the air.

The inventor developed allergies to inside air, and his doctor supplied shots which provided some temporary relief. However, the allergist advised that the shots would have to be taken for the rest of his life. Lifelong allergy shots were not acceptable. A systematic search for an alternative must be made.

A start was in carefully considering the inside air. In most commercial and residential buildings, inside air problems are partially solved by closing off most of the outside air and correcting the temperature of the inside air.

Molds, mildews and various spores grow very rapidly in the moist, dark, cool environment in the air handlers. Also germs, bacteria, viruses, etc. can be retained or multiply in this unhealthy environment.

In an existing hot water/chilled water system in a house with electronic and electrostatic filters, a count of airborne particles measuring 0.5 microns and higher amounted to 5,000 particles in 1/10th of a cubic foot of air in one minute. That high particle count is unacceptable.

The problem is believed to exist because air handling equipment moves large currents of air around a house or office, office building or residential building, and circulates small particles, notably mold and spores, bacteria and viruses, animal dander and other particles, especially below 100 microns, which are not trapped in the filters.

Typically, an air handling system includes large volume intakes with relatively large dimensions and short intake ducts leading to a plenum and then one or more filters below or before one or more heat exchange coils. A chilling coil is often placed at an angle to the horizontal and is usually in the form of finned parallel tubes connected by short semicircular connectors. Condensation which forms on the outsides of the fins, tubes and connectors runs to edges of the coil where it is collected by a drain pan. Exterior condensate runs down the runs and is collected and carried away by the peripheral drain pan and drain. The condensate, drip pan and drain may be a source of moisture which keeps the dark interior of the air handling system damp. Air is inducted through the intake louvers, intake ducts, plenum and heat exchange coils by a blower, usually a high volume, squirrel cage blower driven by an electric motor. The blower increases the kinetic energy of the heated or chilled air and flows the air out through multiple main and branch ducts to wall, floor or ceiling-mounted registers. Often the intake ducts are larger, shorter and fewer than the main and branch distribution ducts.

To promote effective heat transfer between the air and coils, surfaces around the coils are often lined with heat insulating material. To prevent noise transfer from the air handling equipment to the surroundings, the fan chamber may be lined with sound-absorbing materials.

The dark and often damp interiors of the air handling system provide appropriate conditions for the culture of mold, algae and bacteria, and the profligation of spores, bacteria and viruses.

The problem is exacerbated on the downstream sides of heat exchangers or evaporator coils because the relative humidity is increased by chilling the air. Flowing air entrains moisture condensed on the coils and fins. The excess moisture drops out of the air in downstream parts of the air handlers.

The moisture-mold growth problem is acute in heated air systems in which water is wicked or sprayed, in which a water-bathed drum is rotated, and in which water is cascaded and air is blown through a water curtain. The heated air entrains droplets which fall onto or which are condensed onto cooler surfaces, leaving damp interior surfaces downstream of the fan.

A proposed solution provides an ultraviolet light source between the inlet filter and the heat exchange coil. However, much of the system, and especially the downstream parts beyond the coil, are shaded from the growth-terminating effects of the ultraviolet rays. In some conditions, the plant growth within the air handling system is enhanced by the ultraviolet rays in conjunction with the conditions of available moisture and roughened surfaces and shaded areas of the heat transfer and air handling system.

Needs exist for improved air handling systems which reduce and eliminate fine particles, including mold and spores, and other biological particles from air-circulating systems.

SUMMARY OF THE INVENTION

This invention makes the inside surfaces of the air handler compartment, excluding the evaporator coil, fan and motor, anti-fungal. Where inside surfaces are soft, porous insulative-type materials, the present invention covers any such materials plus all other surfaces inside the air handler (excluding the coil, fan and motor) with non-porous material such as metal, foil, Formica, acrylic, plastic, glass, mirror, etc. Any of those appropriate surfaces which were not already high gloss and light colored or white surfaces are covered with a primer and paint such as a high gloss acrylic bright white to produce a dense, non-porous, highly reflective white or light colored surface. The end result is to have anti-fungal surfaces which will prohibit or discourage the growth of mold spores, algae, bacteria, germs, viruses, etc.

Once the inside appropriate surfaces are properly made or corrected, then one or more germicidal light bulbs, which may be high ultraviolet output gas-filled arc tubes with appropriate bases or high ultraviolet output incandescent lamps, are installed inside the air handler compartment. That germicidal or ultraviolet bulb receives its electrical power from the proper wiring in parallel to the electric motor or from an external electric circuit brought into the air handler unit for proper connection. The bulb operates either when the motor operating the fan is energized or continuously, as the specifications or operating manual would dictate. When the germicidal lamp operates with the motor, a delay may be added to start the lamp before or after the motor to smooth power demand.

With the hygienic inside surfaces and the germicidal ultraviolet light bulb, the formation of mold spores, algae, and the uncontrolled growth at atmospheric conditions conducive to this undesirable condition are eliminated or greatly reduced, and healthy air is delivered into the duct system or interior of the building, rather than questionable unhealthy air.

This invention would not change the filters or filtering systems in present use. If particles greater than 300 or 500 microns pass through the filters, then those particles would pass through the air handler and out through the ducts or supply side. The great improvement to be gained from this invention is that the newly formed mold spores, algae, bacteria, germs, viruses, etc. would not be formed as they are being formed in the air handlers in use at this time.

This invention comprises a complete exposure of all air passing through an air handling system immediately before delivery of the air to the distribution and branch ducts, and facilitates the exposure to the ultraviolet radiation by reflecting and scattering the rays throughout the exhaust plenum and head of the intake ducts. The invention also bathes the area downstream of an evaporator coil in bright, reflected ultraviolet rays.

The invention additionally coats all of the surfaces of the exhaust plenum and supply and distribution duct inlet and headers, and the blower intake and exhaust, with highly reflective material, and places an ultraviolet light source within the exhaust plenum to flood the entire exhaust plenum and the supply duct headers of the main supply ducts and/or the entire volume downstream of the heat exchange coil with ultraviolet radiation, which kills, weakens, destroys or greatly reduces any biological material as the material enters or leaves the blower and while the air is being supplied.

Interior surfaces of an air handler unit are coated with a dense, non-porous material, which discourages and prohibits growth of mold, spores, algae, bacteria, germs, viruses and other organisms and microorganisms and allergens. Air is drawn into the air handler unit through a return duct and one or more filters, through a heat exchanger and into a blower within the air handler unit. The blower discharges air through a highly reflective, interiorly coated outlet chamber, where the air is bathed with direct and reflected ultraviolet light. The clean, conditioned air is then delivered through main distribution and supply ducts.

A preferred hygienic air handler apparatus has an air handler enclosure with first and second open ends for respectively connecting to a main return duct and a main distribution supply duct. Successive mounts extend across the enclosure successively from the first end toward the second end for mounting a filter, a heat exchange coil and a blower. Interior surfaces of the enclosure are coated with a dense, non-porous, highly reflective coating for discouraging and prohibiting adherence and growth of mold, algae, bacterial germs, viruses and other organisms, microorganisms and allergens to the dense, non-porous, highly reflective surface coatings.

A preferred hygienic air handler apparatus has one or more ultraviolet light sources installed inside the housing between the blower and the second end of the housing, and/or between the heat exchanger and the blower, for weakening, killing and destroying airborne organisms, microorganisms and allergens in air as it is flowing from the blower through the second end of the housing to the main supply distribution ducts.

A preferred method of supplying hygienic air comprises coating an interior of an air handling enclosure with a dense, non-porous, highly reflective or white material. Air is drawn through a return duct and through a filter into the coated enclosure, and through a heat exchanger and through a chamber where the air is flooded with ultraviolet radiation into a blower. Air is delivered from the blower through an outlet chamber within the enclosure and through air delivery distribution ducts. Air is bathed with ultraviolet light within the outlet chamber.

The outlet chamber is initially coated with a highly reflective material, and ultraviolet light is reflected throughout the outlet chamber.

These and further and other objects and features of the invention are apparent in the disclosure, which includes the above and ongoing written specification, with the claims and the drawings.

DETAILED DESCRIPTION OF THE DRAWINGS

Figure 1:
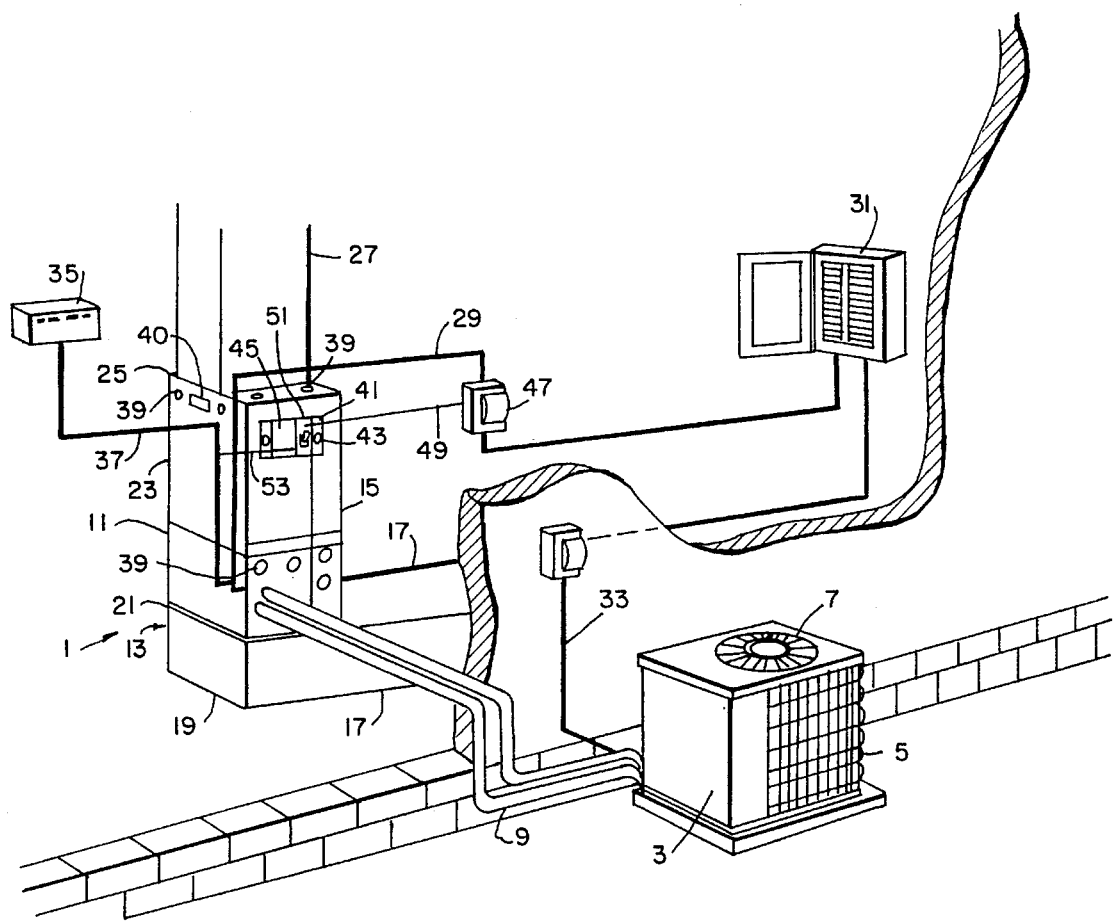
FIG. 1 is an illustration of a typical small office or residential heat pump system with the invention installed.

Referring to FIG. 1, a heating/cooling system is generally indicated by the numeral 1. In this example, the system is a heat pump system. An outside unit 3 has a fan which draws ambient air through an intake 5, blows air through a heat exchanger, and exhausts air through an outlet 7. A compressor within unit 3 compresses a fluid refrigerant and delivers the fluid refrigerant to an air handler.

The heat pump 3 provides either hot compressed liquid or cooled compressed liquid through circulating lines 9 to a heat exchanger inside the heat exchange section 11 of the air handling system 13. A blower in the upper compartment 15 draws air through return duct 17 into the plenum 19 at the bottom of the unit, and then through a filter in section 21, through the heat exchanger in section 11. The blower discharges air into the exhaust plenum 23, and then into the head end 25 of the main distribution duct 27. A blower power supply line 29 leads from an electrical distribution box 31. Power is also supplied power over line 33 to the compressor and the fan in the housing 3.

A thermostat 35 connected to the air handler 13 by a low voltage line 37 controls the operation of the blower in section 15 and controls the compressor and fan in outdoor housing 3.

According to the present invention, the interior of the air handler 13 and the interior walls of the air handler, and particularly the volume downstream of the heat exchanger and of the exhaust plenum 23, are coated with a dense, non-porous, highly reflective coating. One or more sources of ultraviolet rays within the plenum 23. The high density, non-porous surface of plenum 23 prevents growth of microorganisms, mold, algae, bacteria and viruses, and prevents the collection of allergens.

The ultraviolet energy from the ultraviolet sources reflects throughout the exhaust plenum 23 and throughout the head end 25 of the air distribution duct 27, preventing growth and destroying contaminants and allergens as the air moves through those sections.

Power from line 29 is also supplied to ultraviolet lamps which may be mounted on fixtures 39 within the air handler housing. The fixtures are supported on bolts which extend through the housing at any of the places shown by fasteners 39. Windows 40 made of glass used in welders' helmets provide visual access to confirm the interior ultraviolet illumination.

In one embodiment, a plate 41 is mounted by screws 43 around an opening in an accessible outer surface of the distribution plenum 23. The plate-supported ballast 45 is on an outer surface, or alternatively on an inner surface. An ultraviolet source in the form of a gas filled glow discharge tube or an incandescent bulb having high illumination in the ultraviolet range is mounted on the inside of the plate 41. The germicidal tube or incandescent lamp are collectively referred to herein as a ultraviolet bulb or ultraviolet source. An 8 to 15 watt source is acceptable. Higher wattages may be employed.

Power is supplied to the ultraviolet source from the fused junction box 47 over the line 49. The power may be controlled by a switch 51 which is connected to the thermostat by line 53 to turn on and off the ultraviolet source before and after the fan.

Figure 2:
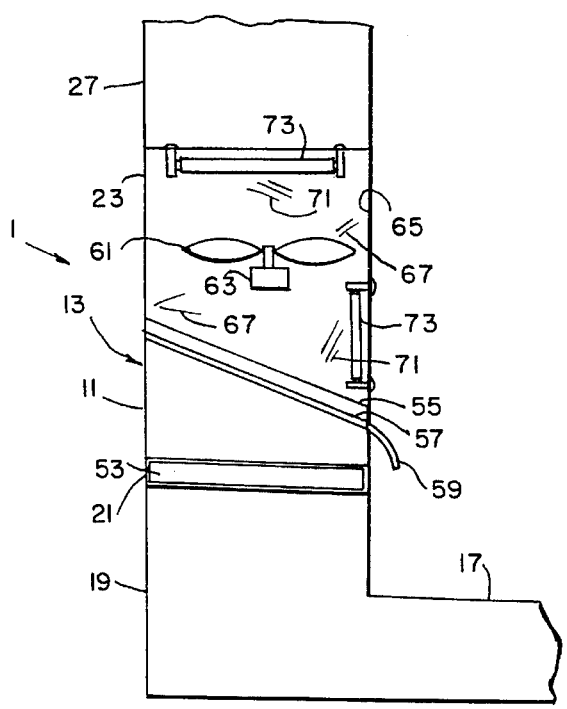
FIG. 2 is a schematic representation of an air handling system with the invention installed.

FIG. 2 is a schematic representation in which similar elements have similar numbers. Return ducts 17 lead to plenum 19. Filter 53 is provided in the filter chamber 21, and a heat exchanger 55 is positioned above the filter in chamber 11. The heat exchange coil is surrounded by a peripheral drip pan 57 to catch condensate, which is removed through a drain 59. A fan schematically represented at 61 is usually a high efficiency squirrel cage blower. Blower 61 is driven by a motor 63, positioned immediately above the heat exchange coil 55 to draw air through the return duct 17 and the return plenum 19, through the filter 53 and the heat exchange coil 55, and to deliver air to the exhaust plenum 23 and the main supply, distribution and branch ducts. The interior of the air handler, and particularly the parts downstream of the heat exchanger and the exhaust plenum 23, are covered with a dense, non-porous, highly reflective surface 65, which prevents the collection of mold and allergens, and which reflects 67 the ultraviolet light energy 71 from source 73.

The ultraviolet energy 71 weakens, kills or destroys airborne organisms. The highly dense, non-porous and reflective surface 65 aids the flooding of the passageway with ultraviolet radiation, and prevents surface accumulation of allergens. The purifying of the air is done effectively as the air leaves the heat exchanger 55 and the blower 61 and passes through the exhaust plenum 23 to the heads of the distribution ducts.

Figure 3:
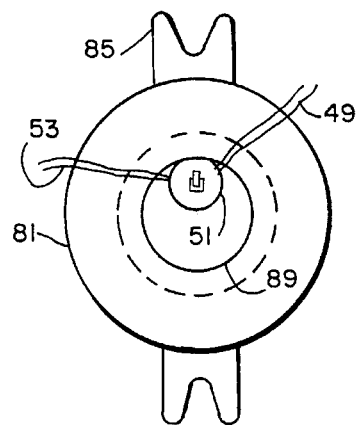
FIGS. 3 and 4 show schematic details of an ultraviolet light mounted on a removable panel.
Figure 4:
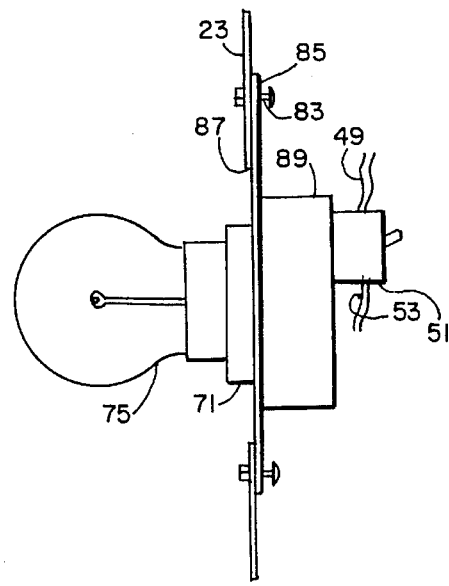

As shown in FIGS. 3 and 4, an incandescent-type ultraviolet light-producing lamp 75 may be mounted in a receptacle 71 on a plate 81 on an end of the housing. Screws 83 are received in bifurcated mounting lugs 85 to mount the plate 81 over an opening 87 in the wall of the exhaust plenum 23. A mount 89 may be supplied on the outside of the plate 81, and a power switch 51, as controlled by lines 53 from the thermostat, controls the application of the power to the lamp from lines 49.

Figure 5:
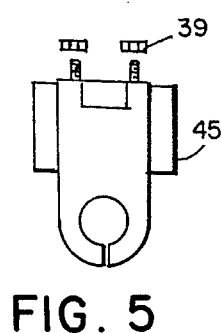
FIG. 5 schematically shows an interior mounting of the ultraviolet source.

In preferred embodiments, the entire receptacles or end mounts for the ultraviolet sources are ultraviolet resistance and are positioned inside the air handler, and are fastened to the walls by fasteners which extend through the walls and which are secured externally by threaded fasteners or by rivets, as shown in FIG. 5.

In new constructions, the dense reflective surface 65, which looks like the interior of a refrigerator, is constructed or coated at the factory. Alternatively, the coating may be supplied at the time of installation.

In retrofitted units, a coating may be applied to the inner walls of the exhaust plenum 23 through access ports or through the openings, such as opening 87, in which the ultraviolet source will be located.

While the invention has been described with reference to specific embodiments, modifications and variations of the invention may be constructed without departing from the scope of the invention, which is defined in the following claims.

I claim:

1. The method of supplying hygienic air, comprising providing an indoor commercial and residential air handler having a coating substantially on all of an interior of the indoor commercial and residential air handler of a high density, non-porous, highly reflective material, drawing the air through a return duct and through a filter into the interiorly coated air handler, drawing air through a heat exchanger evaporator coil where relative humidity of the air is increased by chilling the air, which provides a damp interior providing appropriate conditions for the culture of mold, algae, bacteria and the proliferation of spores, bacteria and viruses, and into a blower, delivering the air from the blower through an outlet chamber within the air handler and through air delivery distribution ducts, and bathing the air with light within the air handler downstream of the heat exchanger, and preventing growth of microorganisms, mold, algae, bacteria and viruses and preventing surface accumulation of allergens.

2. The method of claim 1, wherein the bathing air with light comprises bathing air with ultraviolet light downstream of the heat exchanger evaporator coil.

3. The method of claim 1, wherein the coating further comprises initially coating the entire interior of the air handler with the high density, non-porous, highly reflective coating, and wherein the bathing further comprises reflecting ultraviolet light throughout the air handler downstream of the heat exchanger evaporator coil.

4. The method of claim 1, further comprising initially coating interior walls of the air handler downstream of the heat exchanger with the high density, non-porous, highly reflective coating, and wherein the bathing further comprises reflecting ultraviolet light throughout the walls of the air handler downstream of the heat exchanger.

* * * * *